(12) United States Patent  (10) Patent No.: US 8,976,352 B2
Muraki et al.  (45) Date of Patent: Mar. 10, 2015

(54) MICROPARTICLE ANALYSIS APPARATUS

(75) Inventors: Yosuke Muraki, Tokyo (JP); Masashi Saitoh, Chiba (JP); Shigemi Sakamoto, Chiba (JP)

(73) Assignee: Sony Corporation, Tokyo (JP)

( * ) Notice: Subject to any disclaimer, the term of this patent is extended or adjusted under 35 U.S.C. 154(b) by 407 days.

(21) Appl. No.: 13/370,794

(22) Filed: Feb. 10, 2012

(65) Prior Publication Data

US 2013/0050698 A1 Feb. 28, 2013

Related U.S. Application Data

(60) Provisional application No. 61/528,978, filed on Aug. 30, 2011.

(51) Int. Cl.
*G01N 21/00* (2006.01)
*G01N 15/14* (2006.01)
*G01N 21/64* (2006.01)
*G01N 21/53* (2006.01)

(52) U.S. Cl.
CPC ............ *G01N 15/1427* (2013.01); *G01N 21/64* (2013.01); *G01N 21/53* (2013.01)
USPC ......................................................... 356/338

(58) Field of Classification Search
CPC .................. G01N 15/1427; G01N 2015/1402; G01N 2015/1461; G01N 15/1459; G01R 31/31726; H03M 1/1215
USPC ....................... 356/335–336, 338–343, 72, 73
See application file for complete search history.

(56) References Cited

U.S. PATENT DOCUMENTS

| | | | | |
|---|---|---|---|---|
| 5,150,313 A | * | 9/1992 | van den Engh et al. | 702/79 |
| 5,247,340 A | * | 9/1993 | Ogino | 356/73 |
| 6,239,578 B1 | * | 5/2001 | Schnell et al. | 320/119 |
| 7,057,712 B2 | * | 6/2006 | Beck et al. | 356/72 |
| 7,173,859 B2 | * | 2/2007 | Hemink | 365/185.28 |
| 7,385,694 B2 | * | 6/2008 | Kolp et al. | 356/335 |
| 7,443,491 B2 | * | 10/2008 | Kanda | 356/73 |
| 7,558,943 B2 | * | 7/2009 | Ebisuzaki et al. | 712/10 |
| 7,990,525 B2 | * | 8/2011 | Kanda | 356/73 |
| 8,274,418 B2 | * | 9/2012 | Koli | 341/155 |
| 8,638,792 B2 | * | 1/2014 | Erickson | 370/392 |
| 2005/0219084 A1 | * | 10/2005 | Dietrich et al. | 341/101 |

FOREIGN PATENT DOCUMENTS

| | | |
|---|---|---|
| JP | 2010-503551 | 2/2010 |
| JP | 2010-515055 | 5/2010 |

\* cited by examiner

*Primary Examiner* — Michael A Lyons
*Assistant Examiner* — Shawn Decenzo
(74) *Attorney, Agent, or Firm* — K&L Gates LLP

(57) ABSTRACT

A microparticle analysis apparatus includes at least: a detecting unit having one or a plurality of light sources and a plurality of photodetectors, configured to emit excitation light from the light sources, and to detect light emitted from microparticles on which the excitation light is irradiated, at the photodetectors; a first storage unit configured to store, for each microparticle, data detected at the photodetectors of the detecting unit based on detected time; and a second storage unit configured to store data relating to a particular microparticle of detected data stored in the first storage unit.

5 Claims, 11 Drawing Sheets

MICROPARTICLE ANALYSIS APPARATUS

CROSS REFERENCES TO RELATED APPLICATIONS

The present application claims priority to U.S. Provisional Patent Application 61/528,978 filed in the United States Patent and Trademark Office on Aug. 30, 2011, the entire content of which is hereby incorporated by reference.

BACKGROUND

The present disclosure relates to a microparticle analysis apparatus for optically detecting a specimen such as microparticles or the like, and more specifically, it relates to a microparticle analysis apparatus for detecting multiple light beams regarding one specimen.

In general, in the event of identifying microparticles relating to living bodies such as cells, microorganisms, and liposomes, an optical measurement method using a flow cytometry (flow cytometer) has been employed (e.g., see "Cell Engineering additional volume Experimental Protocol Series Flow Cytometry with Freedom" edited by Hiromitsu Nakauchi, second edition, Shujunsha Co. Ltd. issued on Aug. 31, 2006). This method is a method for identifying multiple microparticles one at a time by a flow cytometry irradiating a laser beam with a particular wavelength on microparticles which make up a row and flow within a flow channel to detect fluorescence or scattered light emitted from the microparticles.

Specifically, a laminar flow is formed of a sample liquid including a microparticle to be measured, and a sheath (capsule) liquid flowing around thereof within a flow channel, and multiple microparticles included in the sample liquid are arrayed in one row. Upon a laser beam being irradiated toward the flow channel in this state, the microparticles passes through the laser beam one at a time so as to traverse the laser beam. At this time, fluorescence and/or scattered light emitted from the microparticles excited by the laser beam is detected by using a photodetector such as a CCD (Charge Coupled Device; charge-coupled device) or PMT (Photo-Multiplier Tube; photomultiplier tube) or the like. The light detected at the photodetector is digitized by being converted into an electric signal, and subjected to statistical analysis, thereby determining the type, size, configuration, and so forth of each of the microp articles.

On the other hand, flow cytometry may detect multiple light beams of which the wavelengths and traveling directions differ regarding one specimen using multiple photodetectors. In such a case, it is difficult to simultaneously detect all of the multiple light beams emitted from the one specimen, and time lag ($\Delta T$) occurs regarding detection of data. However, unless data to be detected at the second and thereafter is confirmed, determination regarding whether or not data detected regarding specimen thereof is pertinent may not be performed.

Therefore, the flow cytometer stores, until all of the light beams are detected regarding each specimen, the data of light detected before the specimen thereof. All of the stored data are read out regarding a specimen determined to be pertinent, and lag of detection time thereof is adjusted, and then processing such as the height of a pulse, calculation of an area, or the like is performed. Also, with a flow cytometer according to the related art, RAM (Random Access Memory) has been used for storage of detected data (see Japanese Unexamined Patent Application Publication (Translation of PCT Application) Nos. 2010-515055 and 2011-503551), and particularly, SRAM (Static Random Access Memory) has been employed.

SUMMARY

However, with SRAM used for a flow cytometer according to the related art, unit price per storage capacity is expensive. For example, in the event of performing measurement by disposing multiple light sources along a flow channel, time lag ($\Delta T$) between detected data is great, and data amount to be stored increases, and accordingly, a plurality of SRAM used for data storage have to be mounted, which makes the apparatus expensive. Also, an FPGA (Field-Programmable Gate Array) including a large capacity of SRAM block may be used as an alternative SRAM, but this is also expensive.

It has been found desirable to provide a microparticle analysis apparatus capable of adjusting lag of detected time of a plurality of data detected regarding one specimen, without increasing costs, even with multiple measurement light sources.

A microparticle analysis apparatus according to an embodiment of the present disclosure includes at least: a detecting unit including one or a plurality of light sources, and a plurality of photodetectors, configured to emit excitation light from the light sources, and to detect light emitted from microparticles on which the excitation light is irradiated, at the photodetectors; a first storage unit configured to store, for each microparticle, data detected at the photodetectors of the detecting unit based on detected time; and a second storage unit configured to store data relating to a particular microparticle of detected data stored in the first storage unit.

The microparticle analysis apparatus may further include a frequency conversion unit configured to down-convert each detected data according to an input frequency before storing in the first storage unit.

The microparticle analysis apparatus may further include a first delay adjustment unit configured to adjust the difference of detected time for each microparticle before storing in the second storage unit.

The microparticle analysis apparatus may further include a computing unit configured to compute one or more of height, width and area of a voltage pulse from detected data stored in the second storage unit.

The microparticle analysis apparatus may further include a second delay adjustment unit configured to adjust the difference of detected time for each microparticle regarding detected data input to the computing unit.

The first storage unit may be SDRAM (Synchronous Dynamic Random Access Memory), and the second storage unit SRAM (Static Random Access Memory) or FPGA (Field Programmable Gate Array).

According to the above configuration, there are provided a first storage unit configured to store data detected at multiple photodetectors provided to the detecting unit for each microparticle based on detected time, and a second storage unit configured to store only data relating to a particular microparticle of the detected data stored in the first storage unit, whereby lag of detected time of a plurality of data detected regarding one specimen can be adjusted without increasing costs even with measurement using multiple light sources.

Additional features and advantages are described herein, and will be apparent from the following Detailed Description and the figures.

DETAILED DESCRIPTION

Embodiments of the present disclosure will be described in detail below with reference to the appended drawings. Note that the present disclosure is not restricted to the embodiments, as described herein. Description will be made in accordance with the following sequence.

1. First Embodiment (example of microparticle analysis apparatus including two types of storage units)
2. Second Embodiment (example of microparticle analysis apparatus including frequency conversion unit)

1. First Embodiment

Overall Configuration of Microparticle Analysis Apparatus

Figure 1:
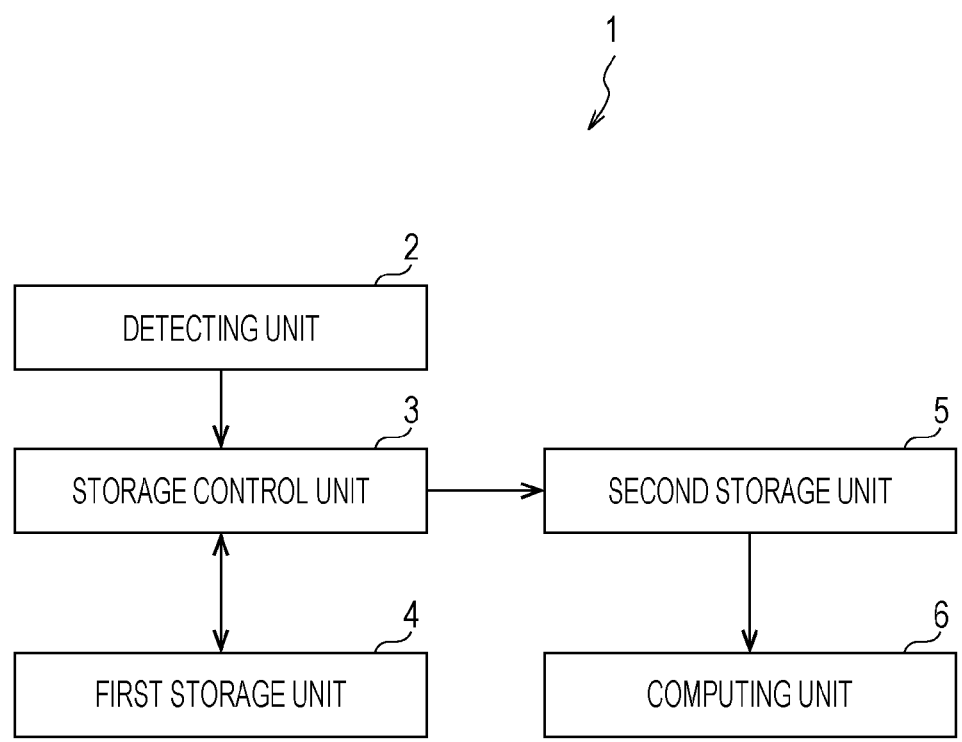
FIG. 1 is a block diagram illustrating the configuration of a microparticle analysis apparatus according to a first embodiment of the present disclosure.

First, description will be made regarding a microparticle analysis apparatus according to a first embodiment of the present disclosure. FIG. 1 is a block diagram illustrating the configuration of the microparticle analysis apparatus according to the present embodiment. The microparticle analysis apparatus 1 according to the present embodiment is an apparatus which irradiates light such as a laser beam on microparticles such as cells, detects light emitted due to that, and analyzes the type, size, configuration, and so forth of a microparticle to be measured.

The term "microparticles" as used here broadly encompasses microparticles relating to living bodies such as cells, microorganisms, and liposomes, or synthetic particles such as latex particles, gel particles, and industrial use particles, or the like. Microparticles relating to living bodies include chromosomes making up various types of cell, liposomes, mitochondria, and organellas (cell organelles), and so forth. Also, cells include plant cells, animal cells, and blood cells and so forth. Further, microorganisms include bacteria such as *Escherichia coli*, viruses such as tobacco mosaic virus, and fungus such as yeast fungus. Let us say that the microparticles relating to living bodies may also include polymers relating to living bodies such as nucleic acid, protein, and complexes of these.

On the other hand, examples of industrial use particles include particles made up of an organic polymer material, an inorganic material, or a metal material. Examples used as an organic polymer material include polystyrene, styrene, divinylbenzen, and polymethylmethacrylate. Also, examples used as an inorganic material include glass, silica, and a magnetic material. Examples used as a metal material include gold colloid, and aluminum. Note that the shapes of these microparticles have generally a globular shape, but may have a non-globular shape, and also the size, mass, and so forth are also not restricted in particular.

As shown in FIG. 1, the microparticle analysis apparatus 1 according to the present embodiment includes at least a detecting unit 2 which detects light emitted from microparticles, and two types of storage units (first storage unit 4, second storage unit 5) which store detected data detected at the detecting unit 2. Also, with this microparticle analysis apparatus 1, if appropriate, there may be provided a storage control unit 3 which controls data to be stored in the first storage unit 4 and second storage unit 5, or a computing unit 6 which performs computing processing of the detected data stored in the second storage unit 5.

Detecting Unit 2

The detecting unit 2 includes a single or multiple light sources, and multiple photodetectors, and detects fluorescence or scattered light emitted from microparticles. The light source used here can be selected according to the contents of measurement or the like as appropriate, but examples of this include a laser diode, an SHG (Second Harmonic Generation) laser, a gas laser, and a high-intensity LED (Light Emitting Diode: luminous diode). Also, the photodetectors are not restricted in particular as long as being capable of detecting fluorescence or scattered light emitted from microparticles. Examples thereof include a PD (Photo diode), CCD (Charge Coupled Device), PMT (Photo-Multiplier Tube), and a power meter.

Storage Control Unit 3

The storage control unit 3 stores the data detected at the multiple photodetectors provided to the detecting unit 2 in the first storage unit 4, and also reads out the detected data of a particular microparticle from the data stored in the first storage unit 4, and stores in the second storage unit 5. At this time, the storage control unit 3 performs coarse adjustment of time difference ($\Delta T$) of the detected data for each microparticle.

First Storage Unit 4

The first storage unit 4 temporarily stores the data detected at the multiple photodetectors provided to the detecting unit 2 for each microparticle based on detected time, and can be configured of, for example, SDRAM (Synchronous Dynamic Random Access Memory). SDRAM is DRAM which operates in sync with a clock signal with a certain cycle, and has features such that the transfer speed of data is fast, and SDRAM is cheaper than DRAM. If SDRAM is applied to this first storage unit 4, the detected data of each microparticle can be written in an address according to time difference ($\Delta T$) thereof in the detected sequence, whereby delay adjustment can be readily performed with high precision.

Second Storage Unit 5

The second storage unit 5 extracts and stores, of the detected data stored in the first storage unit 4, only data relating to a microparticle determined to be pertinent, and can be configured of, for example, SRAM (Static Random Access Memory) or FPGA (Field Programmable Gate Array), and particularly, SRAM is preferably used. If the first storage unit 4 is configured of SDRAM, the resolution of $\Delta T$ is restricted by ROW access thereof, but if SRAM is used as the second storage unit 5, finer time adjustment can be performed.

Computing Unit 6

The computing unit 6 computes the height (peak), width (width), area (integral), or the like of a voltage pulse based on the detected data of each of the microparticles stored in the second storage unit 5. Thus, the computing unit 6 can determine the type, size, configuration, and so forth of the microparticle thereof. Note that the computing unit 6 may additionally perform computation processing such as integration of the detected data, calculation of a mean value of the detected data of all of the microparticles, or the like.

Operation

Next, the operation of the above-described microparticle analysis apparatus 1 will be described with a case where the first storage unit 4 is configured of SDRAM, and the second storage unit 5 is configured of SRAM as an example. With the microparticle analysis apparatus 1 according to the present embodiment, multiple light sources are disposed along a flow channel, multiple laser beams (excitation light) with a different wavelength are irradiated from these light sources, and multiple light beams emitted from one microparticle 10 are detected by the multiple photodetectors.

Figure 2:
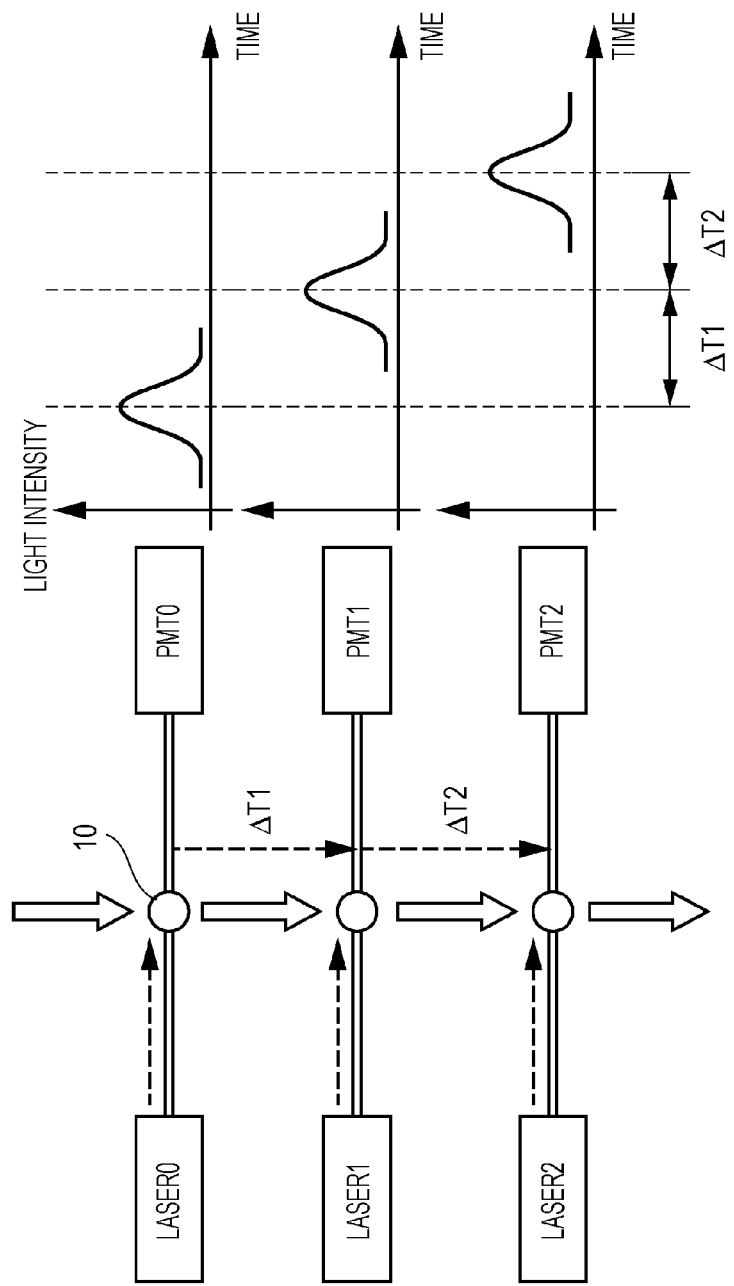
FIG. 2 is a diagram illustrating a relation between a laser spot and an optical signal at a detecting unit.
Figure 3:
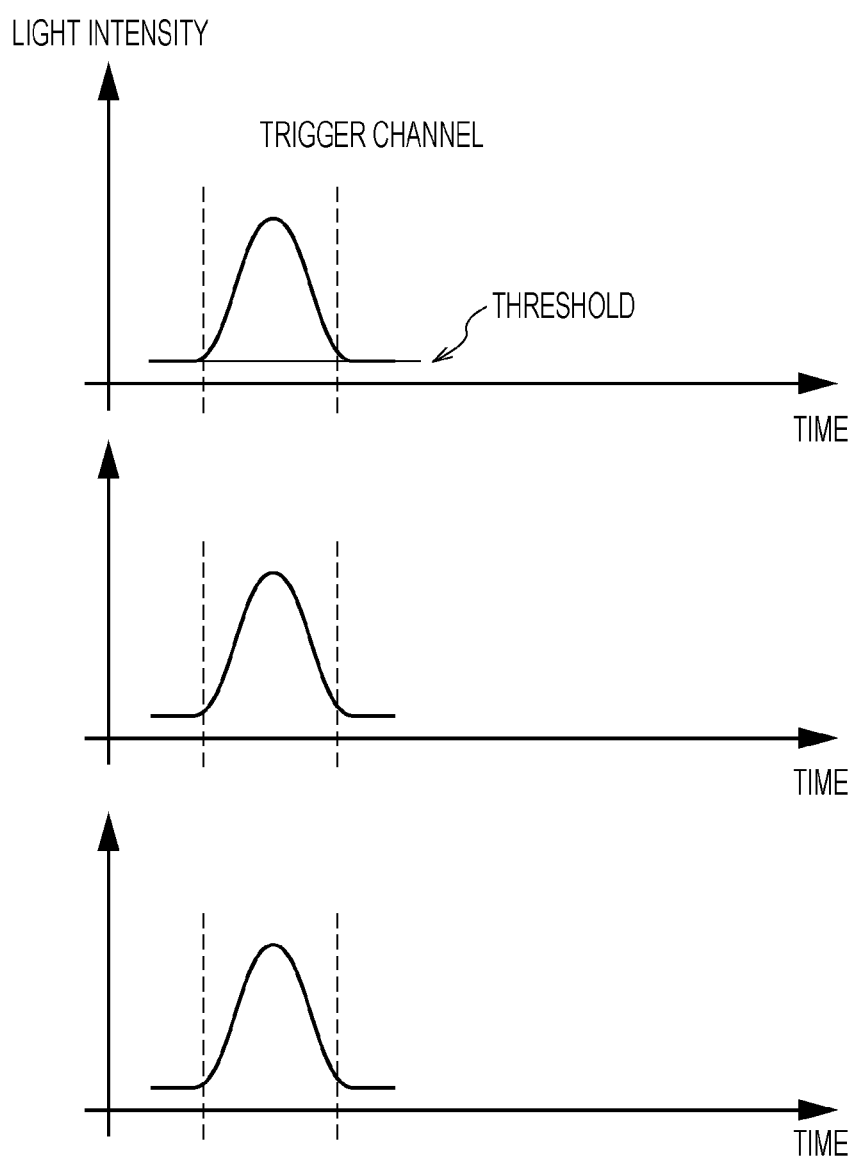
FIG. 3 is a diagram illustrating the operation of a computing unit.
Figure 4:
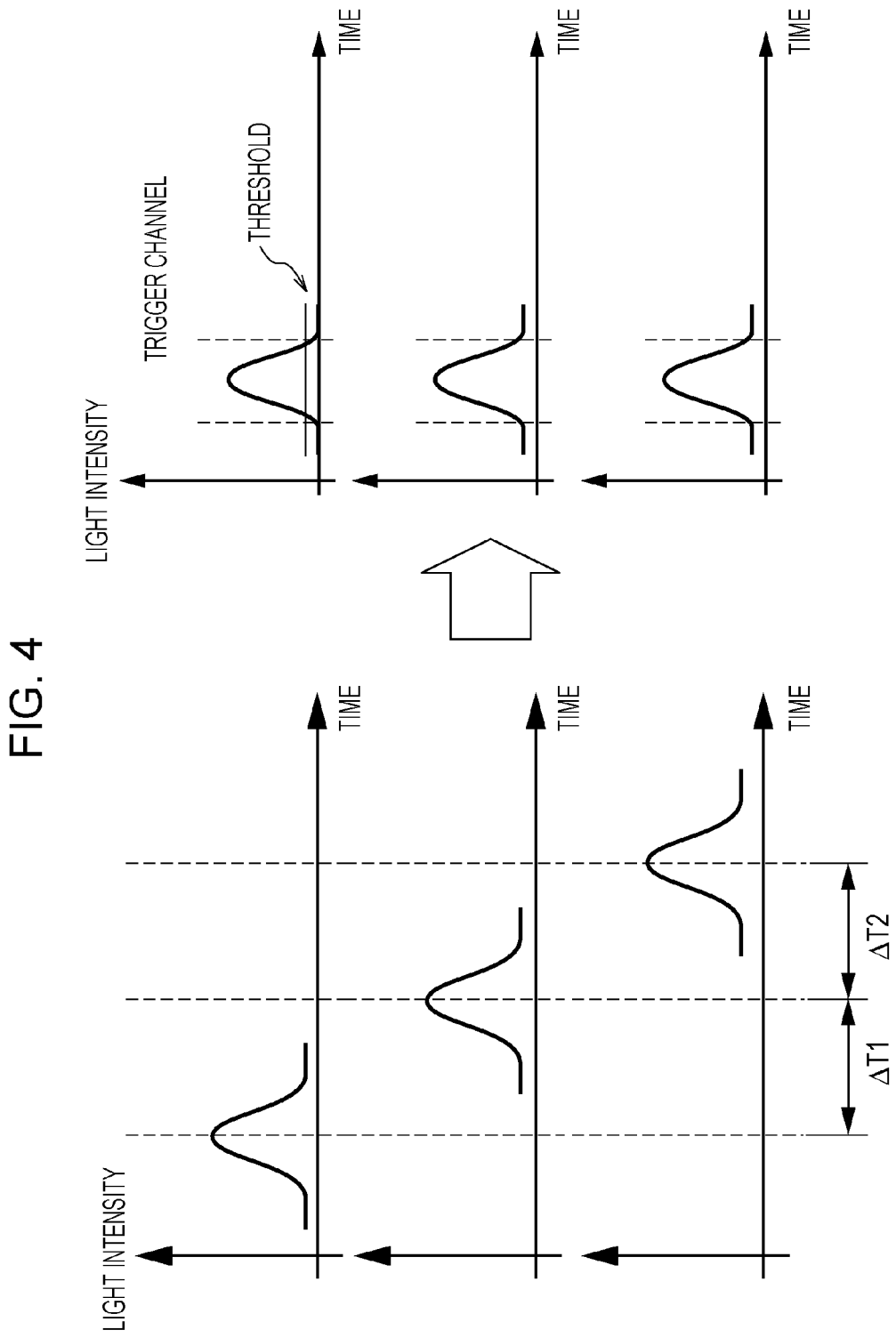
FIG. 4 is a diagram illustrating detected data before and after delay adjustment.
Figure 5:
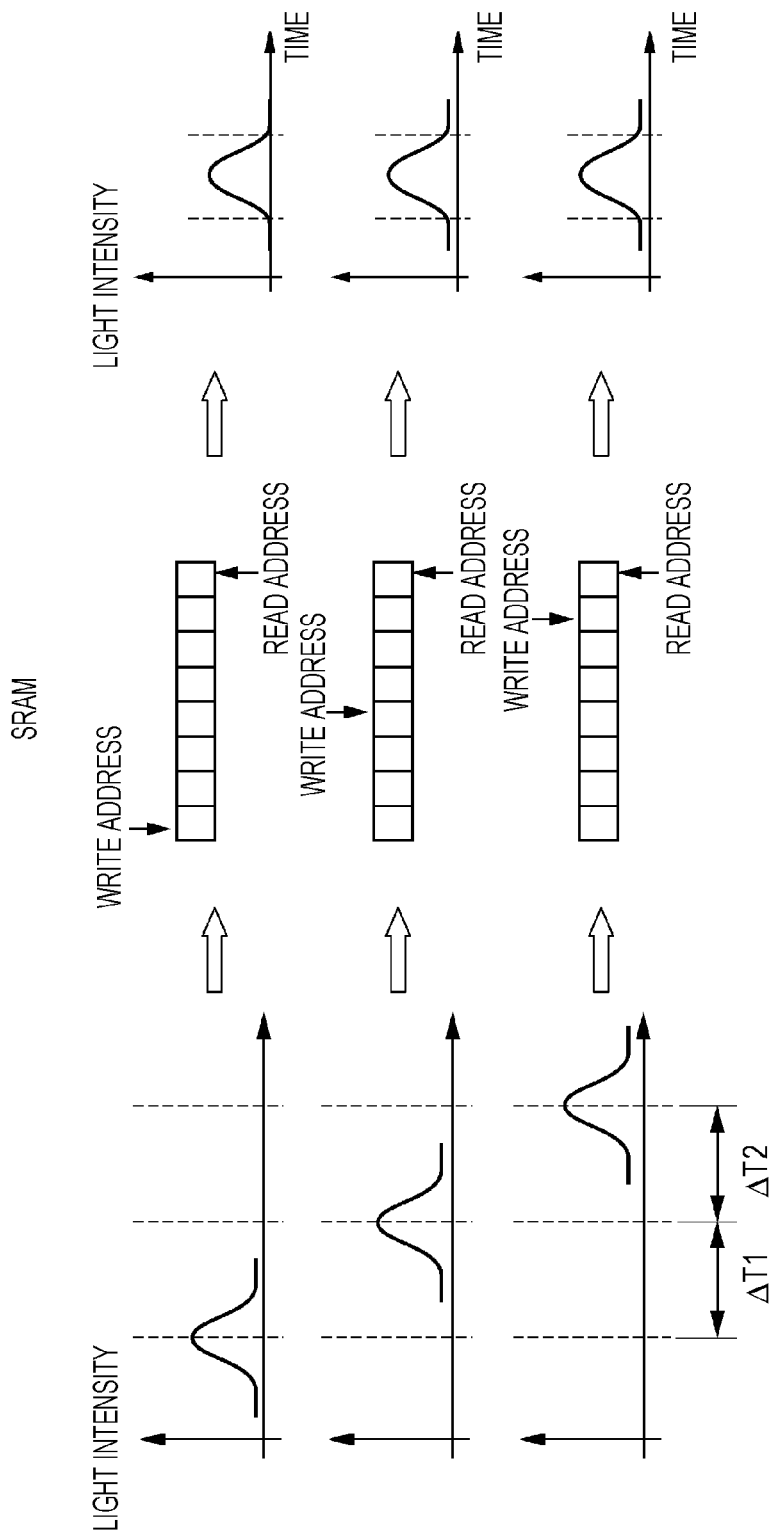
FIG. 5 is a diagram illustrating delay adjustment method according to the related art.

FIG. 2 is a diagram illustrating a relation between a laser spot and an optical signal in the detecting unit 2, and FIG. 3 is a diagram illustrating the operation of the computing unit 6. Also, FIG. 4 is a diagram illustrating detected data before and after delay adjustment, and FIG. 5 is a diagram illustrating delay adjustment method according to the related art. In this case, as shown in FIG. 2, the microparticle 10 passes through the laser spots with time difference ($\Delta T$). Lag also occurs regarding timing detected by the photodetectors, and time difference ($\Delta T$) also occurs regarding emergence of a pulse. Here, the time difference ($\Delta T$) is determined in proportion to the flow speed of the microparticle 10.

On the other hand, with the computing unit 6, during a period while the optical signal (detected data) selected by a trigger channel exceeds a threshold, area, height, and width information and so forth of another channel are computed. That is to say, in order to correctly calculate all of the information, as shown in FIG. 3, it is desirable for all of the pulses detected regarding the microparticle 10 to be positioned at the same time. In order to achieve this, as shown in FIG. 4, emergence time difference of pulses occurring for each laser spot, i.e., detected time difference ($\Delta T$) has to be adjusted before input to the computing unit 6.

Note that, with a microparticle analysis apparatus according to the related art, as shown in FIG. 5, an SRAM buffer is provided for each channel, and a write address or read address is adjusted, thereby adjusting the time difference ($\Delta T$). However, with this method, the detected data amount increases, and a larger capacity of SRAM has to be used.

Figure 6:
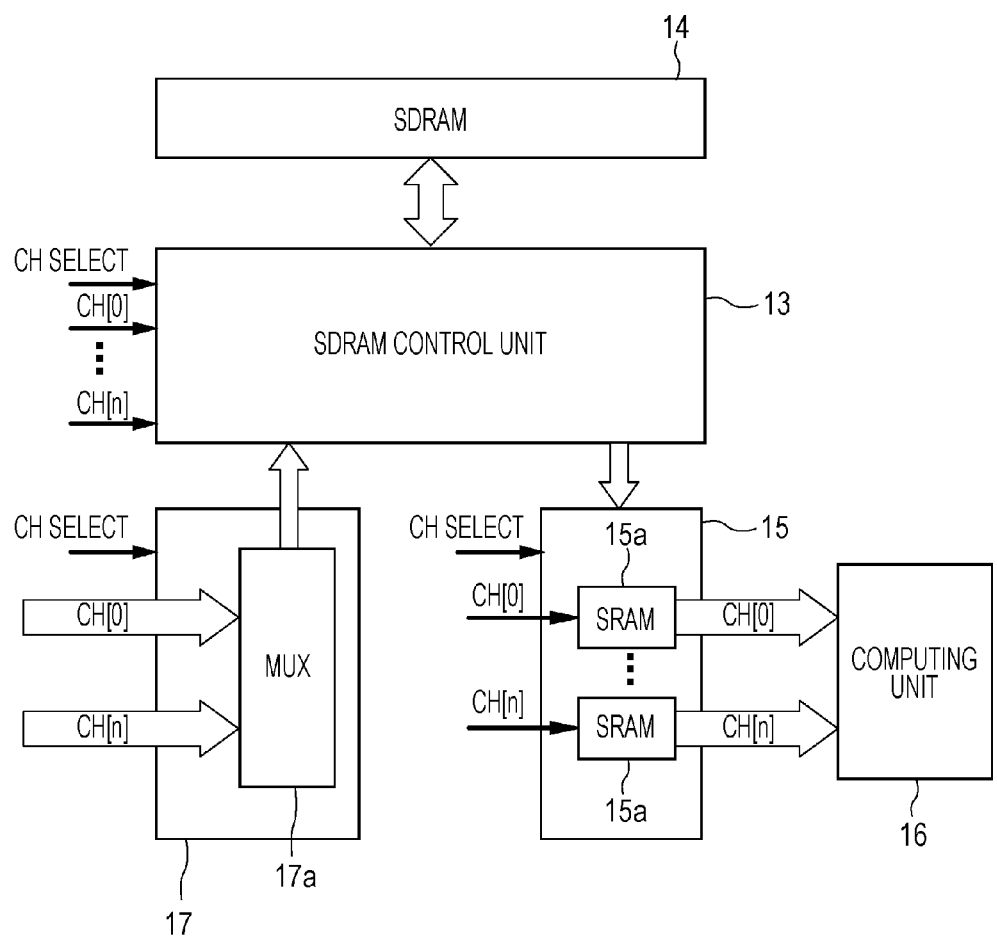
FIG. 6 is a diagram illustrating the operation of the microparticle analysis apparatus shown in FIG. 1.

Therefore, with the microparticle analysis apparatus 1 according to the present embodiment, two types of storage devices of SDRAM and SRAM are used, thereby performing delay adjustment at high speed and high precision without increasing costs. FIG. 6 is a diagram illustrating the operation of the microparticle analysis apparatus 1 shown in FIG. 1. Specifically, as shown in FIG. 6, the optical signals detected at the photodetectors are input to the SDRAM control unit 13 via an FIFO (First In, First Out) type circuit 17 including a multiplexer (MUX) 17a in accordance with the detected sequence.

The optical signal input to the SDRAM control unit 13 is stored in a predetermined address of the SDRAM 14 according to the detected time for each microparticle 10. After all of the optical signals are recorded regarding one microparticle 10, determination is made whether or not the data is pertinent, and only the data of the microparticle 10 determined to be pertinent is read out by the SDRAM control unit 13, and stored in each SRAM 15a mounted on the FPGA 15.

Figure 7A:
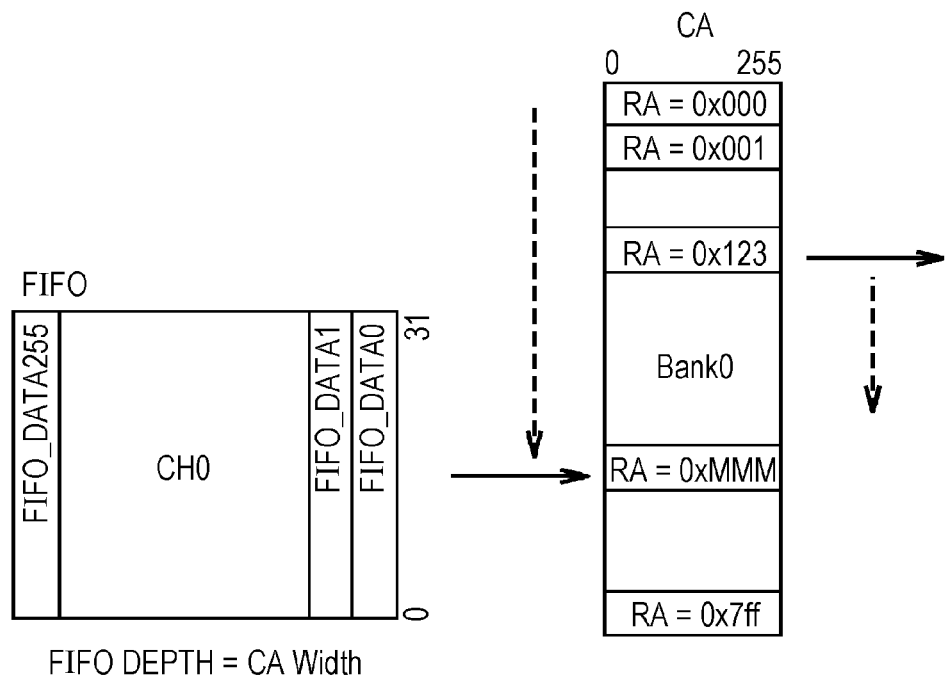
FIGS. 7A and 7B are diagrams illustrating coarse adjustment and fine adjustment methods.
Figure 7B:
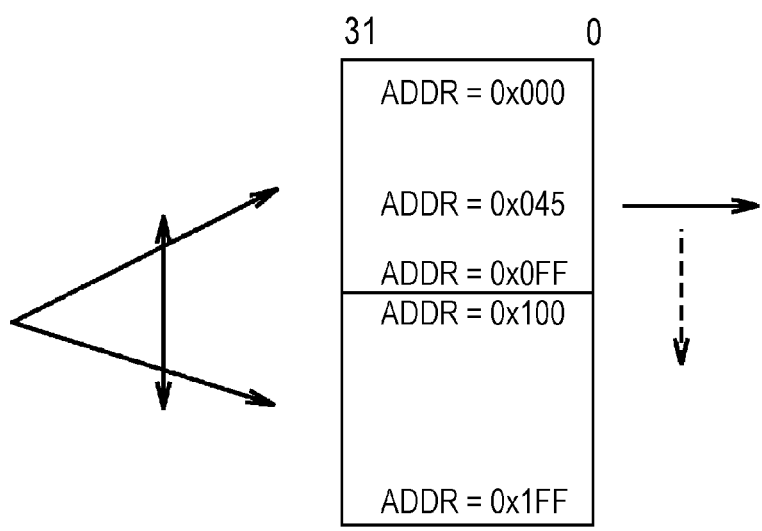

At that time, the SDRAM control unit 13 performs coarse adjustment of the detected time difference ($\Delta T$). FIGS. 7A and 7B are diagrams illustrating coarse adjustment and fine adjustment methods in time difference adjustment. This coarse adjustment is performed, for example, as shown in FIG. 7A, by adjusting a row address (Row Address) read out from the SDRAM 14. Specifically, the SDRAM control unit 13 stores column address (Column Address) worth of data in the FIFO 17, and performs full page burst writing (Full Page Burst Write) in order from RA =0×000. At this time, the row address is incremented (Increment) to 0 following RA Max (0×7 FF in the case of FIG. 7A). CH of which the set value of delay adjustment is 0×123** then sequentially reads out from the row address =0×123.

Also, the optical signals stored in each SRAM 15a mounted on the FPGA 15 are fine-adjusted regarding the detected time difference ($\Delta T$), and then input to the computing unit 16. This fine adjustment is performed, for example, as shown in FIG. 7B, by the address read out from the SRAW 15a being adjusted. Here, the data read out from the SDRAM 14 is stored in each SRAM 15a, but at this time, in order to prevent an address before writing from being read out, the depth of the SRAM 15a is prepared double of column addresses (Column Address) (9 bits in the case of FIG. 7B). CH of which the set value of delay adjustment is 0x***45 then sequentially reads out from the address=0x045.

Thereafter, the computing unit 6 computes the height (peak), width (width), area (integral), or the like of a voltage pulse based on the delay-adjusted optical signal.

As described above in detail, with the microparticle analysis apparatus 10 according to the present embodiment, based on the detected time, the detected data is stored in the first storage unit for each microparticle, and accordingly, even when the detected data amount is great, the time difference ($\Delta T$) of the detected data can readily be adjusted with high precision. In particular, SDRAM is used as the first storage unit, and SRAM is used as the second storage, whereby delay adjustment can be performed with low costs without deteriorating the resolution.

2. Second Embodiment

Overall Configuration of Microparticle Analysis Apparatus

Figure 8:
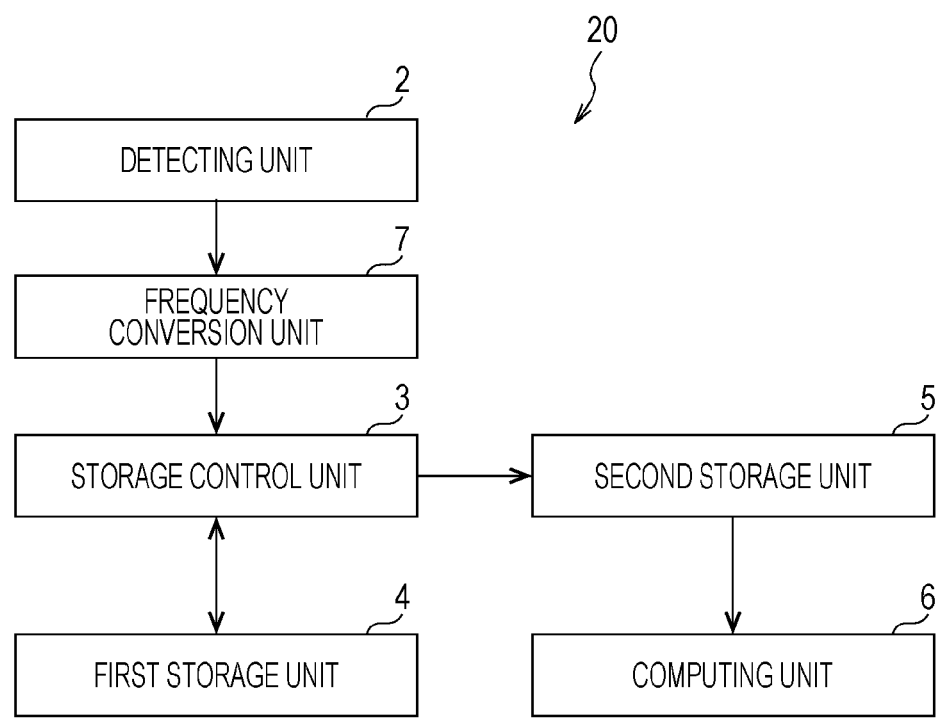
FIG. 8 is a block diagram illustrating the configuration of a microparticle analysis apparatus according to a second embodiment of the present disclosure.

Next, a microparticle analysis apparatus according to the second embodiment of the present disclosure will be described. FIG. 8 is a block diagram illustrating the configuration of the microparticle analysis apparatus according to the present embodiment. Note that, in FIG. 8, the same components as the components of the microparticle analysis apparatus 1 according to the first embodiment shown in FIG. 1 are denoted with the same reference numerals, and detailed description thereof will be omitted.

With a microparticle analysis apparatus 20 according to the present embodiment, there is provided a frequency conversion unit 7 which down-converts each detected data according to the input frequency before storing in the first storage unit 4. Also, it is desirable from the standpoint of improvement in detected precision to provide a decimation filter for removing noise components to this microparticle analysis apparatus 20.

Frequency Conversion Unit 7

The frequency conversion unit 7 is a unit for down-converting the optical signal detected at the detecting unit 2 to reduce the amount of data to be stored in the first storage unit, and with the microparticle analysis apparatus 20 according to the present embodiment, for example, the data of 100 MHz is down-converted to 10 MHz.

Decimation Filter

The decimation filter is a filter for removing noise components from the optical signal detected at the detecting unit 2, and is disposed in front of the frequency conversion unit 7. For example, in the event that the data of 100 MHz is down-converted to 10 MHz by the above frequency conversion unit 7, a low-pass filter of 5 MHz is employed.

Operation

Figure 9:
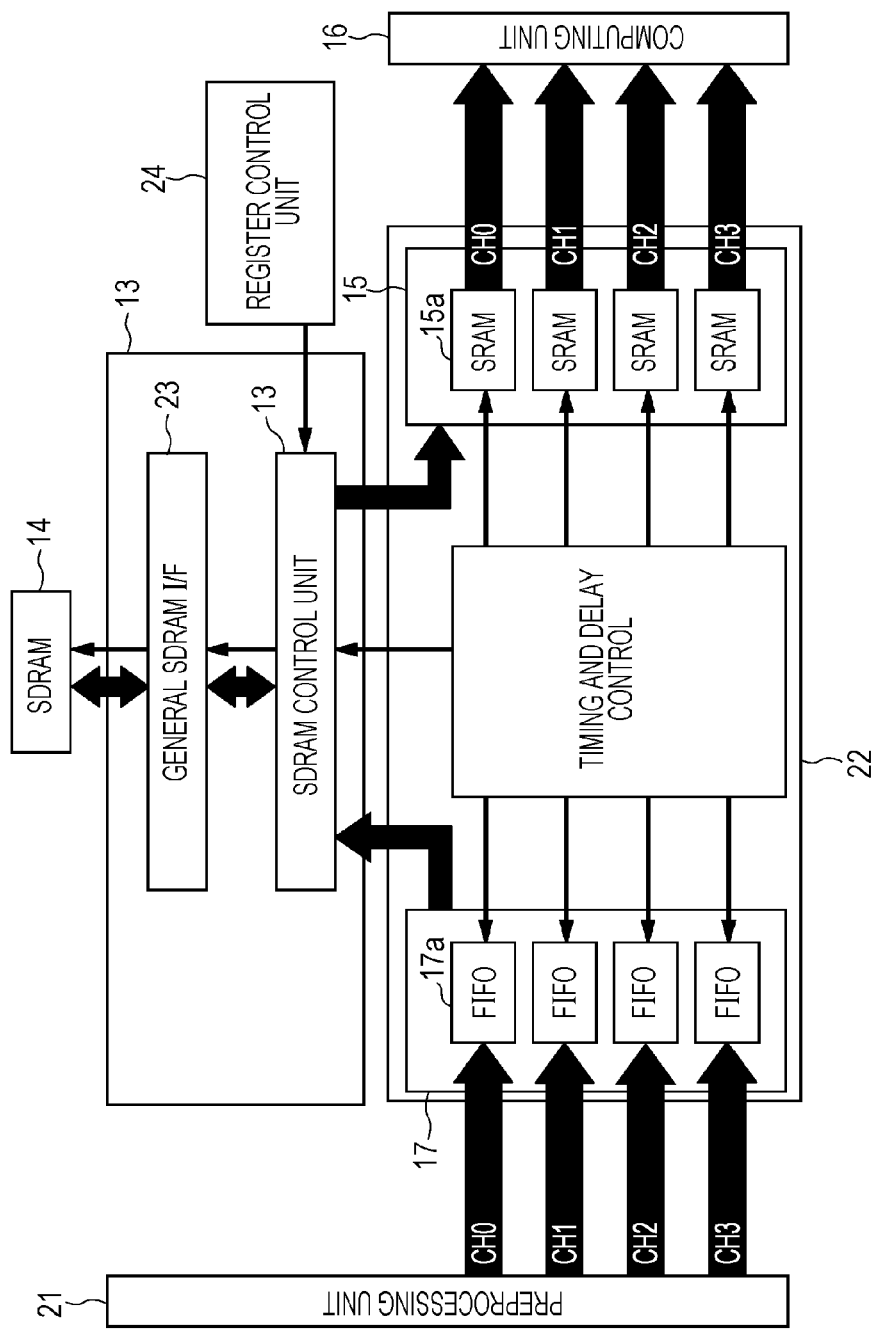
FIG. 9 is a diagram illustrating a specific configuration example of the microparticle analysis apparatus shown in FIG. 8, and operation thereof.
Figure 10A:
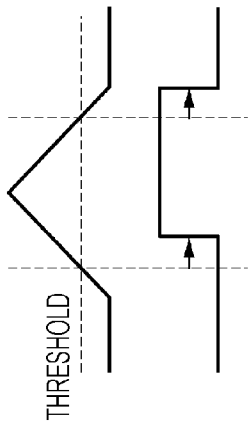
FIGS. 10A through 10C are diagrams illustrating the outline of the processes shown in FIG. 9.
Figure 10B:
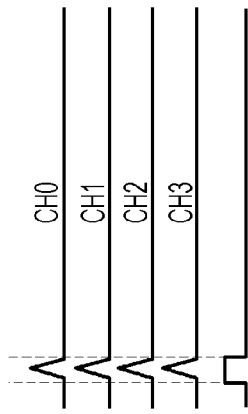
Figure 10C:
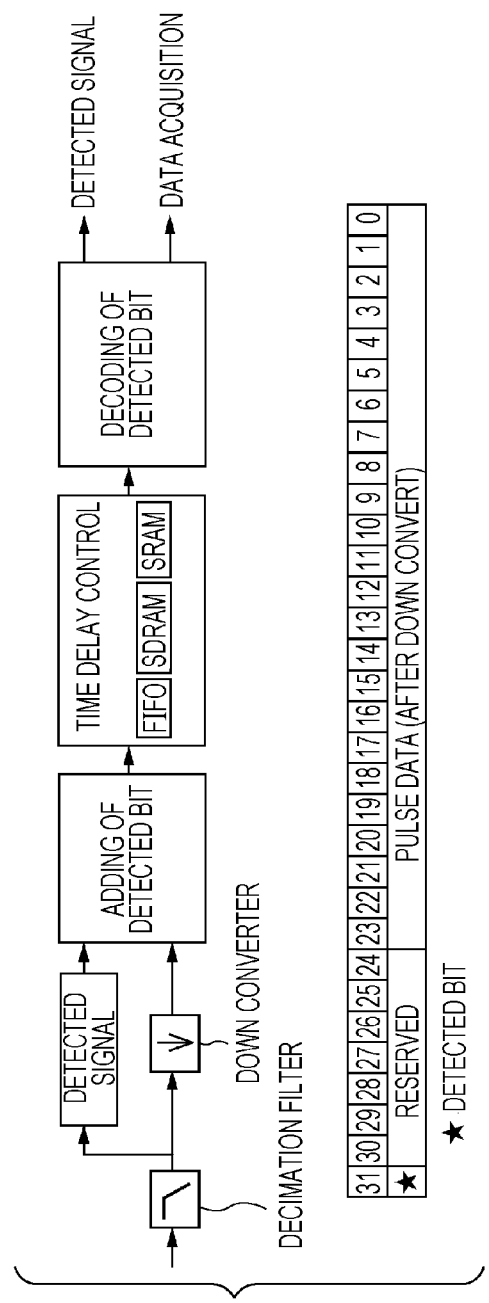
Figure 11:
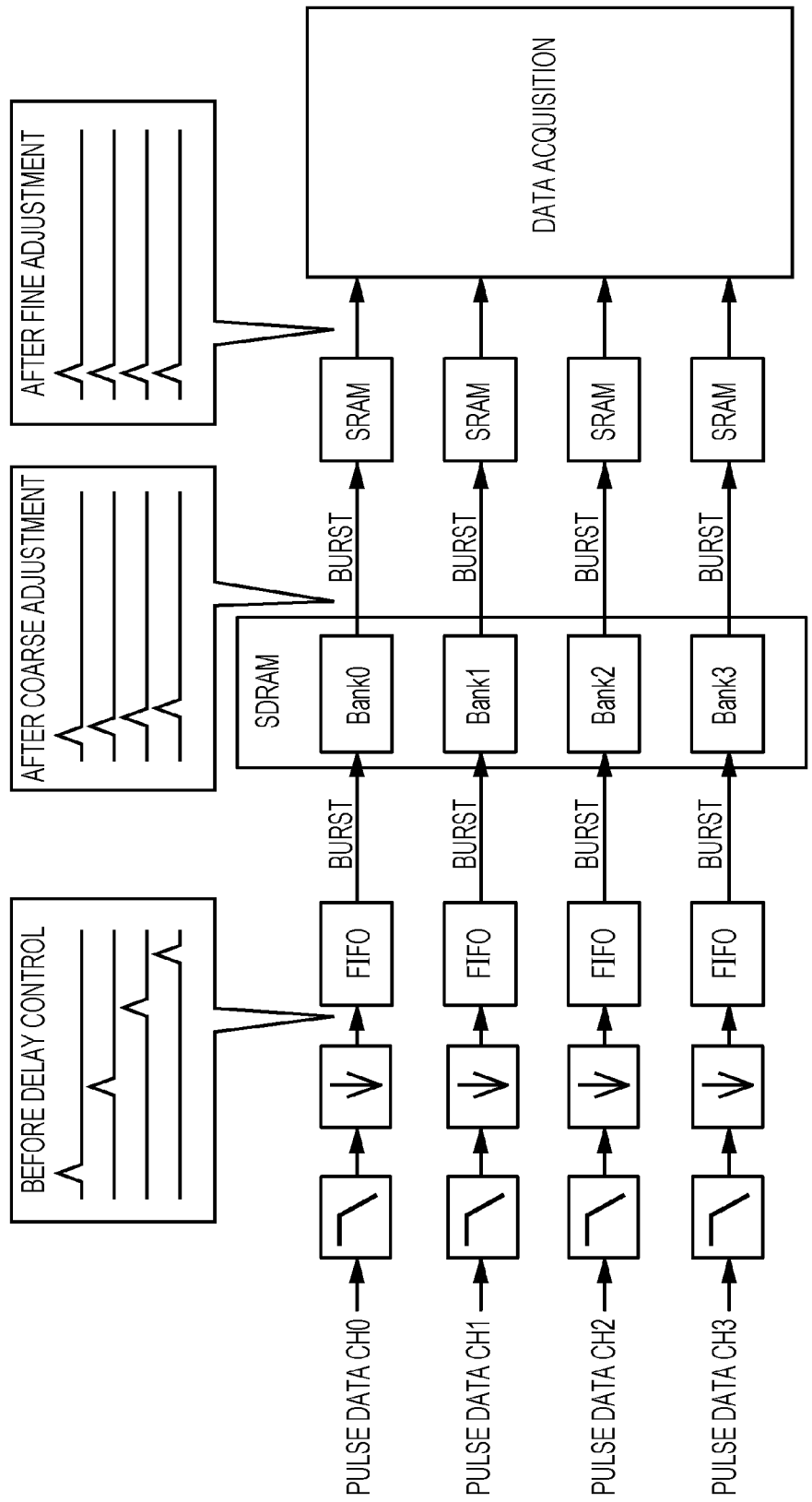
FIG. 11 is a diagram illustrating the delay adjustment method shown in FIGS. 10A through 10C.

Next, the operation of the microparticle analysis apparatus 20 according to the present embodiment will be described. FIG. 9 is a diagram illustrating a specific configuration example of the microparticle analysis apparatus 20 shown in FIG. 8, and operation thereof, and FIGS. 10A through 10C are diagrams illustrating the outline of each process. Also, FIG. 11 is a diagram illustrating a method of delay adjustment shown in FIGS. 10A through 10C. The microparticle analysis apparatus 20 according to the present embodiment may have a configuration such as shown in FIG. 9, for example. In this case, the frequency conversion unit 7 is provided to a preprocessing unit 21.

The preprocessing unit 21 removes, as shown in FIG. 10C, noise components from the optical signal detected at the detecting unit 2 (detected data) by the decimation filter, and then generates a detected signal. With regard to generation of a detected signal, as shown in FIG. 10B, detection is performed when the number of samples having a threshold or more is equal to or greater than a certain value so as not to detect noise. It is desirable from the perspective of detected precision to perform this signal detection before down conversion by the frequency conversion unit 7. On the other hand, as shown in FIG. 10A, the signals of all of the channels are calculated based on the signal of a trigger channel, but there is a case where a signal detected delay in a time-axial manner is used as a trigger signal, and accordingly, it is desirable to generate a trigger signal after delay adjustment.

As shown in FIG. 11, with the microparticle analysis apparatus 20 according to the present embodiment as well, in the same way as with the above-described first embodiment, detected time difference ($\Delta T$) is adjusted in two stages. Specifically, optical signals CH0 through CH3 processed at the preprocessing unit 21 are input to the SDRAM control unit 13 via the FIFO-type circuit 17a of the delay adjustment unit 22 in the detected order. The optical signal input to the SCRAM control unit 13 is stored in a predetermined address of the SDRAM 14 according to detected time via the SDRAM interface 23 for each microparticle 10.

After all of the optical signals are recorded regarding one microparticle 10, determination is made whether or not data thereof is pertinent, and only the data of the microparticle 10 determined to be pertinent is read out by the SDRAM control unit 13, and stored in each SRAM 15a mounted on the FPGA 15. At this time, coarse adjustment of the detected time difference ($\Delta T$) is performed based on the delay adjustment value stored in the register control unit 24.

With this microparticle analysis apparatus 20 as well, writing and readout as to the SDRAM is performed with full page burst (Full Page Burst) for each row address (Row Address). Therefore, in order to adjust resolution within a column address (Column Address), SRAM is disposed in the subsequent stage. Thus, delay (detected time difference $\Delta T$) can be fine-adjusted by address adjustment at the time of readout.

Note that it is difficult to obtain consistency between an address and time response if different channels exist in the same bank. For example, in the event that the data of the same time is read out regarding multiple channels, it is difficult to obtain consistency unless offset is added to an address. Therefore, it is desirable to suppress the number channels of data input from the preprocessing unit 21 to equal or smaller than the number of banks of writing as to the SDRAM.

As described above in detail, with the microparticle analysis apparatus 20 according to the present embodiment, the frequency conversion unit is provided, and the information amount to be input to the first storage unit 4 is reduced, whereby access within time can be performed even when the detected data amount is great. Note that this arrangement is particularly effective in the case that the data (analog) of a source does not have the information of a band equal to or greater than that, i.e., in the event that the first storage unit 4 has the I/F configured of sufficiently fast SDRAM, the frequency conversion unit 7 does not have to be provided. Also, an arrangement and an advantage other than those described above in the microparticle analysis apparatus 20 according to the present embodiment are the same as those described in the first embodiment.

Note that the present disclosure may have the following configurations.

(1) A microparticle analysis apparatus includes at least: a detecting unit, which includes one or a plurality of light sources and a plurality of photodetectors, configured to emit excitation light from the light sources, and to detect light emitted from microparticles on which this excitation light is irradiated, at the photodetectors; a first storage unit configured to store, for each microparticle, data detected at the photodetectors of this detecting unit based on detected time; and a second storage unit configured to store only data relating to a particular microparticle of detected data stored in this first storage unit.

(2) The microparticle analysis apparatus in (1) may further include a frequency conversion unit configured to down-convert each detected data according to an input frequency before storing in the first storage unit.

(3) The microparticle analysis apparatus in (1) or (2) may further include a first delay adjustment unit configured to adjust the difference of detected time for each microparticle regarding the detected data stored in the first storage unit.

(4) The microparticle analysis apparatus in any of (1) through (3) may further include a computing unit configured to compute one or more of height, width and area of a voltage pulse from detected data stored in the second storage unit.

(5) The microparticle analysis apparatus in (4) may further include a second delay adjustment unit configured to adjust the difference of detected time for each microparticle regarding detected data input to the computing unit.

(6) In any of (1) through (5), the first storage unit may be SDRAM (Synchronous Dynamic Random Access Memory), and the second storage unit SRAM (Static Random Access Memory) or FPGA (Field Programmable Gate Array).

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A microparticle analysis apparatus, comprising at least:
a detecting unit, including
one or a plurality of light sources, and
a plurality of photodetectors,
configured to emit excitation light from said light sources, and to detect light emitted from microparticles on which said excitation light is irradiated, at said photodetectors;
a first storage unit configured to store, for each microparticle, data detected at the photodetectors of said detecting unit based on detected time, the first storage unit comprising a synchronous dynamic random access memory (SDRAM);
a second storage unit configured to store data relating to a particular microparticle of detected data stored in said first storage unit, the second storage unit comprising a static random access memory (SRAM) or a field programmable gate array (FPGA), and the first and second storage units respectively configured to store delay-adjusted optical signals of the particular microparticle; and a first delay adjustment unit operatively coupled to the first storage unit and configured to adjust the detected time for each microparticle before storing in the second storage unit such that the detected time has a non-zero difference between the plurality of photodetectors.

2. The microparticle analysis apparatus according to claim 1, further comprising:

a frequency conversion unit configured to down-convert each detected data according to an input frequency before storing in said first storage unit.

3. The microparticle analysis apparatus according to claim 1, further comprising:

a computing unit configured to compute one or more of height, width and area of a voltage pulse from detected data stored in said second storage unit.

4. The microparticle analysis apparatus according to claim 1, further comprising:

a second delay adjustment unit configured to adjust the difference of detected time for each microparticle regarding detected data.

5. The microparticle analysis apparatus according to claim 1, wherein said storage unit is SDRAM.

* * * * *